United States Patent [19]

Buffington et al.

[11] Patent Number: 5,728,178
[45] Date of Patent: Mar. 17, 1998

[54] GUIDE TUBE FOR GASTROSTOMY TUBE PLACEMENT

[75] Inventors: C. A. Tony Buffington, Worthington; John V. Mauterer; Sarah K. Abood, both of Columbus, all of Ohio

[73] Assignee: The Ohio State University, Columbus, Ohio

[21] Appl. No.: 296,856

[22] Filed: Aug. 26, 1994

Related U.S. Application Data

[63] Continuation of Ser. No. 37,034, Mar. 25, 1993, abandoned.
[51] Int. Cl.$^6$ .................. A61F 2/54; A61M 5/00
[52] U.S. Cl. .................. 623/66; 604/115; 604/116
[58] Field of Search .................. 623/11, 66; 604/521, 604/116, 270, 264, 281, 282, 275, 278, 115; 138/DIG. 8, 177, 178; 606/108, 109, 115, 119, 122, 123, 127, 129; 128/898

[56] References Cited

U.S. PATENT DOCUMENTS

| | | | |
|---|---|---|---|
| 3,800 | 10/1844 | Gale | 604/264 |
| 2,024,982 | 12/1935 | Scott | 606/108 |
| 2,259,488 | 10/1941 | Raiche | 604/281 |
| 2,400,251 | 5/1946 | Nagel | 606/119 |
| 3,175,557 | 3/1965 | Hammond | 604/264 |
| 3,623,511 | 11/1971 | Levin | 138/177 |
| 3,685,509 | 8/1972 | Bentall | 606/119 |
| 3,719,209 | 3/1973 | Rush et al. | 138/177 |
| 3,719,737 | 3/1973 | Vaillancourt et al. | 604/281 |
| 3,729,008 | 4/1973 | Berkovits | 604/281 |
| 3,777,743 | 12/1973 | Binard et al. | 606/119 |
| 3,805,301 | 4/1974 | Liebig | 623/1 |
| 3,908,637 | 9/1975 | Doroshow | 604/104 |
| 3,926,192 | 12/1975 | Van Maren | 606/119 |
| 3,957,055 | 5/1976 | Linder et al. | 606/108 |
| 4,037,627 | 7/1977 | Hurst | 138/177 |
| 4,225,979 | 10/1980 | Rey et al. | 623/12 |
| 4,239,264 | 12/1980 | Evans | 138/177 |
| 4,432,758 | 2/1984 | Finegold | 604/278 |
| 4,571,239 | 2/1986 | Heyman et al. | 604/54 |
| 4,573,576 | 3/1986 | Krol | 604/104 |
| 4,636,346 | 1/1987 | Gold et al. | 138/177 |
| 4,642,092 | 2/1987 | Moss | 604/280 |
| 4,687,471 | 8/1987 | Twardowski et al. | 604/280 |
| 4,925,445 | 5/1990 | Sakamoto et al. | 604/281 |
| 4,968,296 | 11/1990 | Ritch et al. | 606/108 |
| 4,981,477 | 1/1991 | Schon et al. | 604/264 |
| 4,998,754 | 3/1991 | Matsumoto et al. | 138/177 |
| 5,016,640 | 5/1991 | Ruiz | 604/281 |
| 5,053,022 | 10/1991 | Bryant et al. | 604/275 |
| 5,080,650 | 1/1992 | Hirsch et al. | 604/104 |
| 5,084,033 | 1/1992 | O'Neill et al. | 604/282 |
| 5,098,413 | 3/1992 | Trudell et al. | 604/281 |

(List continued on next page.)

OTHER PUBLICATIONS

Bright et al., "Percutaneous Endoscopic Tube Gastrostomy In Dogs", *Am. J. Vet. Res.*, vol. 49, No. 5, 1988, pp. 629–633.
Fulton et al., "Blind Percutaneous Placement of a Gastrostomy Tube for Nutritional Support in Dogs and Cats" *JAVMA*, vol. 201, No. 5, 1992, pp. 697–699.

*Primary Examiner*—Debra S. Brittingham
*Attorney, Agent, or Firm*—Frank H. Foster; Kremblas, Foster, Millard & Pollick

[57] ABSTRACT

A hollow, rigid guide tube has a bend nearer to one end than the opposite end. The bent end of the guide tube is inserted through an animal's mouth and esophagus, and into its stomach. The bent end is pressed against the interior of the animal's stomach by manipulating the opposite end which extends out of the animal's mouth. A needle is pushed through the animal's skin and into the stomach end of the guide tube. A fiber is passed through the needle and into and through the whole guide tube. The fiber then extends from outside the animal's abdomen through the stomach wall, through the esophagus and out the animal's mouth. The guide tube and needle are removed and a gastrostomy tube is fastened to the mouth end of the fiber and is pulled into the stomach sidewall in the conventional manner. The guide tube preferably has an outwardly flared surface at one end and has an annular disk attached near the opposite end of the tube.

5 Claims, 1 Drawing Sheet

U.S. PATENT DOCUMENTS

| | | | |
|---|---|---|---|
| 5,139,486 | 8/1992 | Moss | 604/264 |
| 5,168,864 | 12/1992 | Shockey | 604/280 |
| 5,178,623 | 1/1993 | Cinberg et al. | 606/108 |
| 5,183,470 | 2/1993 | Wettermann | 604/281 |
| 5,188,120 | 2/1993 | White et al. | 33/512 |
| 5,201,882 | 4/1993 | Paxon | 623/23 |
| 5,215,540 | 6/1993 | Anderhub | 604/264 |
| 5,217,466 | 6/1993 | Hasson | 606/119 |

5,728,178

GUIDE TUBE FOR GASTROSTOMY TUBE PLACEMENT

This is a continuation of application Ser. No. 08/037,034, filed Mar. 25, 1993, now abandoned.

TECHNICAL FIELD

This invention relates broadly to the field of medical devices used in the process of inserting a gastrostomy tube in the stomach wall of an animal, and more specifically relates to devices for aiding in the process of passing a fiber from outside the abdomen, through the wall of the animal's stomach and out of the mouth. The fiber is later used to pull the gastrostomy tube through the mouth, esophagus and stomach of the animal and into its desired position in the stomach wall in the conventional manner.

BACKGROUND ART

A gastrostomy tube is a short, thin tube which is inserted in the abdomen of an animal and which extends from the exterior of the animal's body through the skin, through the stomach wall, and into the interior of the stomach. The gastrostomy tube is used as a passageway to the stomach to provide nutrients or medication directly to the stomach of an animal which cannot or will not eat.

The conventional method of installing gastrostomy tubes is to make a small incision in the animal's skin and push a needle and a surrounding sheath through the skin and stomach wall of the animal. A fiber is then fed through the needle and into the stomach of the animal. An endoscope is placed in the animal's stomach through the mouth and esophagus and is used to visually determine whether the fiber has passed into the stomach and where in the stomach it is located. A four-pronged snare extends similarly into the stomach of the animal, and is used to pull one end of the fiber out of the animal's body to be accessible at the mouth. A gastrostomy tube is then attached to the mouth end of the fiber and pulled into the stomach and then through the incision and needle hole.

One problem with the conventional method is that not all surgeons desiring to perform this operation possess all the proper equipment, such as an endoscope, which is necessary to view the location of the fiber within the stomach. Another problem is the difficulty of locating and grasping the fiber in the stomach.

Therefore, the need exists for a device which increases the ease and simplicity of the installation of gastrostomy tubes, and provides a less expensive and therefore more available way of installing a gastrostomy tube.

BRIEF DISCLOSURE OF INVENTION

A guide tube apparatus is extended from an animal's mouth through the esophagus and into the animal's stomach for aiding in the insertion of a gastrostomy tube in the animal. The guide tube comprises a hollow, rigid tube, a minor portion of which has its axis bent away from the axis of the remaining, major portion. This bent region forms an elbow nearer to one end of the tube.

A method of inserting a fiber from an animal's mouth through its stomach to outside the animal comprises inserting a hollow, rigid tube through the mouth and esophagus and into the stomach of the animal. The tube extends from outside the mouth of the animal and into the stomach of the animal where the tube has a minor portion which is bent away from the axis of the remaining, major portion of the tube. The end of the tube within the stomach is positioned against the wall of the stomach and pressed outwardly by manipulating the opposite end of the tube protruding from the animal's mouth. The location and orientation of the tip of the tube is adjusted by palpating the abdomen. A hollow needle is then inserted through the animal and into the end of the tube that is within the animal's stomach. A fiber is guided through the needle, into and through the tube, and out of the opposite end of the tube at the animal's mouth.

Figure 1:
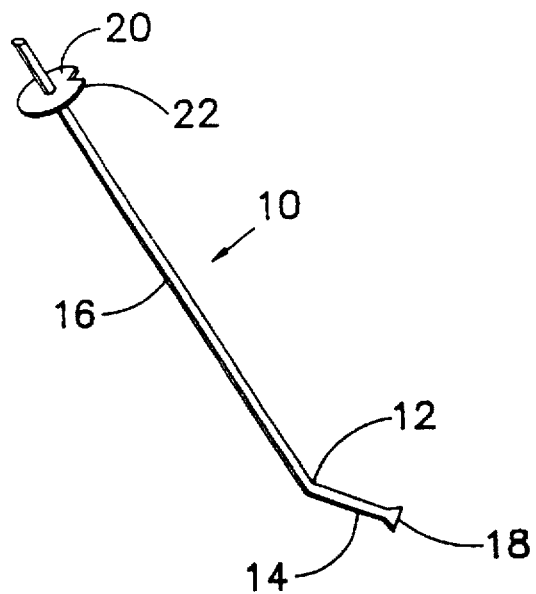
FIG. 1 is a view in perspective illustrating the preferred embodiment of the present invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

FIG. 1 shows a preferred guide tube 10 which is approximately 40 cm in overall length and approximately 5 mm in tube outer diameter. The guide tube 10 is preferably made of a hollow, cylindrically-shaped, thin-walled, stainless steel pipe. The tube 10 can alternatively be made of plastic or other types of suitable metals and materials.

The tube 10 has an elbow 12 formed near one end. The elbow 12 is a bend in the guide tube 10 forming an angled minor portion 14 of the tube 10. The axis of the minor portion 14 of the guide tube 10 is angled with respect to the axis of a major portion 16 of the guide tube 10. Preferably, the angle between the two axes is 45°. However, it is only necessary that a slight angle exist at some position along the length of the guide tube 10 in order for the guide tube 10 to function as described below.

The end of the guide tube 10 nearest the elbow 12 has an outwardly flared, bell-shaped end 18. The flared end 18 is larger in diameter than the rest of the guide tube 10. The surface of the flared end 18 is angled to direct objects which contact the inner surface of the flared end 18 into the interior of the guide tube 10.

An annular disk 20 may be attached to the exterior circumferential surface of the guide tube 10 near the end of the guide tube 10 farthest from the elbow 12. The axis of the disk 20 is preferably coaxial with the axis of the major portion 16 of the guide tube 10. A marking, preferably a notch 22 formed in the outer circumferential surface of the disk 20, is formed on the disk 20 to indicate the direction that the minor portion 14 of the guide tube 10 bends away from the major portion 16.

The guide tube 10 shown in FIG. 1 has the preferred dimensions and proportions to be used with an average sized cat.

Figure 2:
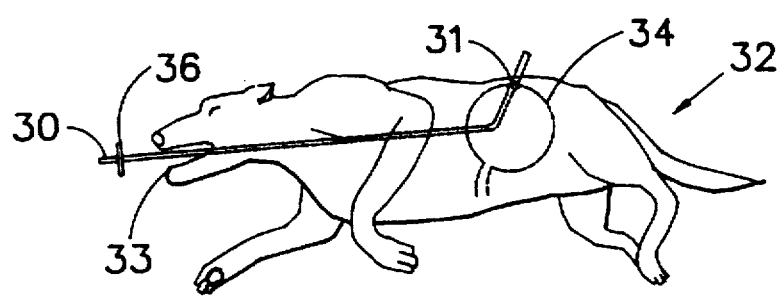
FIG. 2 is a view in perspective illustrating the position of a guide tube (shown with hidden lines) within an animal.

FIG. 2 shows a different guide tube 30 inserted within an animal 32 in its preferred orientation during use. The guide tube 30 shown in FIG. 2 appears identical to the guide tube 10 used in FIG. 1. However, since the guide tube 30 is being used in a dog, it is most likely of larger dimensions, yet still proportioned to, the guide tube 10 which is for use with average sized cats. The guide tube 30 extends through a mouth 33 and esophagus (not shown) of the animal 32 and into a stomach 34. A minor portion end 31 of the guide tube 30 is within the animal's stomach 34 and the opposite end of the guide tube 30 extends outside of the body of the animal 32.

An annular disk 36 is attached to the guide tube 30 for indicating the direction in which the elbow end 31 of the guide tube 30 is bent when that end is not visible. The disk also provides a place on which a label or trademark may be imprinted. Alternatively, a mark, such as a shallow groove, can be cut into the outer wall of the tube to mark the bend direction.

The outwardly flared surface of the minor portion end 31 is pressed against the wall of the stomach 34 by manipulating the end of the guide tube 30 that is outside of the animal's body. A person's hand feels for the minor portion end 31 of the guide tube 30 pressing against the interior of the stomach 34 which can be palpated on the exterior of the animal's abdomen. While manipulating the exterior end of the guide tube 30 with one hand, the person locates the opposite end 31 of the guide tube 30 by feel. Once the person suitably locates and positions this minor portion end 31, he or she inserts a hollow needle through the animal's skin and into the minor portion end 31.

Figure 3:
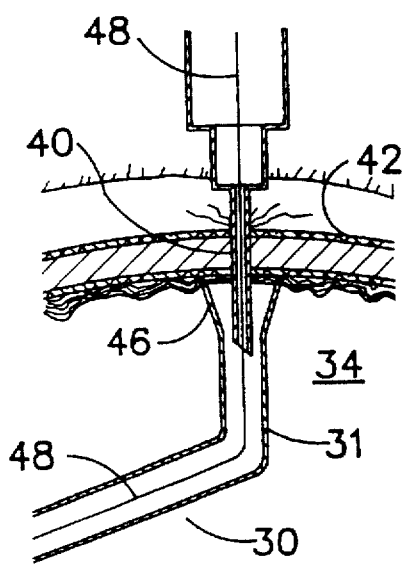
FIG. 3 is an enlarged view in section illustrating the region of FIG. 2 in which a needle protrudes through an animal's skin, into the interior of its stomach, and extends into a guide tube.

In the enlarged view of FIG. 2, shown in FIG. 3, a needle 40 extends through an animal's skin 42 and into the animal's stomach 34. The guide tube 30 is pressed against the wall of the stomach 34 and directs the needle 40 into its interior when the needle 40 contacts an outwardly flared end surface 46. A fiber 48 is then inserted into the needle 40 and pushed through the needle 40 and into the guide tube 30. The guide tube 30 extends through the animal's stomach, esophagus and mouth. The fiber 48 is pushed completely through the guide tube 30 and comes out the mouth end of the guide tube 30 which is outside the animal's body (shown in FIG. 2). The guide tube 30 is then removed from within the animal, the needle 40 is removed from the animal's skin 42 and the fiber is left in place.

A conventional gastrostomy tube is tied to the mouth end of the fiber 48 and is pulled through the animal's mouth, esophagus and stomach by pulling on the fiber 48. The gastrostomy tube is then pulled through a small incision in the animal's side to enlarge the opening as is conventionally done and is fastened into place.

The preferred guide tube 10 shown in FIG. 1 is rigid, which is defined for purposes of this invention as the characteristic of having sufficient stiffness to allow a person or machine to manipulate one end of the guide tube 10 outside of an animal's body while pressing the opposite end of the guide tube 10 outwardly against the inner wall of the animal's stomach so its flared end can be palpated on the abdomen. Some small amount of flexibility is allowed, and of course, is always present. However, the guide tube 10 must be stiff enough that it will not deflect under the force of manipulation so much that the end opposite the manipulated end cannot force the stomach wall outwardly enough to be felt by a person's hand or a motion sensing machine.

The preferred guide tube 10 is made of stainless steel which typically has rigidity characteristics making it sufficiently rigid for the present invention. However, it is possible to use certain plastics to form a guide tube, the rigidity of which is of primary concern. A hard plastic, for example polyvinyl chloride, would probably be sufficiently rigid to be used in the present invention. A very soft plastic, such as surgical tubing which flexes under its own weight, would not be rigid enough for the present invention.

The flared end 18 of the guide tube 10 shown in FIG. 1 is not necessary to practice the present invention. A guide tube without a flared end 18 would function similarly to the preferred embodiment, but the flared end 18 increases the guiding of a needle into the interior of the guide tube 10. It is also not necessary to attach the disk 20 as shown in the preferred embodiment, but it is preferable due to the advantages it provides.

The preferred dimensions of the present invention have been indicated and are meant as a general guide for tubes used in particularly sized animals, specifically average sized cats. However, if the present invention is to be used on a larger animal such as a dog or a horse, a larger tube having proportionately larger dimensions would obviously be necessary. Additionally, if the present invention is to be used on a smaller animal such as a rabbit or a gerbil, a guide tube with smaller dimensions will need to be used. For any use, the guide tube should be long enough that when it is inserted in its desired position with one end pressing against the side wall of the stomach and the opposite end manipulated by a person or machine, a significant length of guide tube should protrude out of the animal's mouth in order to provide a sufficient handle for manipulation. The guide tube may also be used in humans.

While certain preferred embodiments of the present invention have been disclosed in detail, it is to be understood that various modifications may be adopted without departing from the spirit of the invention or scope of the following claims.

We claim:

1. A guide tube for insertion in an animal having a mouth, an esophagus and a stomach connected in series communication, for extending from the animal's mouth, through the esophagus into the animal's stomach and for aiding in the insertion of a gastrostomy tube in the animal, the apparatus comprising: a hollow, rigid tube having an interior wall contoured for guiding an end of a fiber pushed through the tube, an insertion end of the tube having an interior wall and a longitudinal axis bent away from a longitudinal axis of an opposite, handle end of the tube, the tube being at least as long as the distance from the mouth to the stomach, the tube having an outer diameter no greater than the esophagus, and the interior wall of the insertion end of the tube contoured outwardly from the insertion end axis, forming an angle with the axis less than 90 degrees to form a flared end.

2. An apparatus in accordance with claim 1 wherein an annular disk is mounted on an outer surface of the tube near the second end of the tube.

3. An apparatus in accordance with claim 2 wherein a mark is formed on the disk to indicate the direction in which the minor portion of the tube bends away from the major portion.

4. An apparatus in accordance with claim 3 wherein the angle formed between the axis of the minor portion of the tube and the axis of the major portion of the tube is approximately 45°.

5. An apparatus in accordance with claim 4 wherein an outer diameter of the tube is approximately 5 mm and an overall length of the tube is approximately 40 cm.

\* \* \* \* \*